(12) United States Patent
Verdooner et al.

(10) Patent No.: US 7,854,510 B2
(45) Date of Patent: Dec. 21, 2010

(54) APPARATUS AND METHOD FOR IMAGING THE EYE

(76) Inventors: Steven Roger Verdooner, 7615 Sierra Dr., Granite Bay, CA (US) 95746; Steven Leach, 17634 Penny Ct., Grass Valley, CA (US) 95949-7238

(*) Notice: Subject to any disclaimer, the term of this patent is extended or adjusted under 35 U.S.C. 154(b) by 0 days.

(21) Appl. No.: 12/580,247

(22) Filed: Oct. 15, 2009

(65) Prior Publication Data

US 2010/0097573 A1   Apr. 22, 2010

Related U.S. Application Data

(60) Provisional application No. 61/105,901, filed on Oct. 16, 2008.

(51) Int. Cl.
*A61B 3/10* (2006.01)
*A61B 3/14* (2006.01)

(52) U.S. Cl. .................. 351/214; 351/206; 351/221; 351/246

(58) Field of Classification Search ............... 351/214, 351/206, 221, 209, 210, 211, 212, 213, 246
See application file for complete search history.

(56) References Cited

U.S. PATENT DOCUMENTS

| | | | | |
|---|---|---|---|---|
| 5,220,360 | A | * 6/1993 | Verdooner et al. | 351/212 |
| 5,993,001 | A | * 11/1999 | Bursell et al. | 351/212 |
| 7,118,217 | B2 | * 10/2006 | Kardon et al. | 351/206 |

* cited by examiner

*Primary Examiner*—Hung X Dang
(74) *Attorney, Agent, or Firm*—Michael Ries

(57) ABSTRACT

A slit lamp mounted eye imaging device for viewing wide field and/or magnified views of the retina or the anterior segment through an undilated or dilated pupil. The apparatus images posterior and anterior segments of the eye, and sections/focal planes in between and contains an illumination system that uses one or more LEDs, shifting optical elements, and/or aperture stops where the light can be delivered into the optical system on optical axis or off axis from center of optical system and return imaging path from the retina, thereby creating artifacts in different locations on retina. Image processing is employed to detect and eliminate artifacts from images. The device is well suited for retinal imaging through an undilated pupil, non-pharmacologically dilated, or a pupil as small as 2 mm. Two or more images with reflection artifacts can be created and subsequently recombined through image processing into a composite artifact-free image.

32 Claims, 4 Drawing Sheets

APPARATUS AND METHOD FOR IMAGING THE EYE

REFERENCE TO RELATED APPLICATIONS

This patent application claims the benefit of U.S. Provisional Application No. 61/105,901 filed on Oct. 16, 2008, the disclosure of which is incorporated herein in its entirety by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates generally to imaging a person's eye and more specifically to imaging the anterior segment including the cornea, lens and anterior chamber of the eye, the posterior segment of the eye including the ocular fundus for imaging modalities such as color fundus, fluorescein angiography, ICG angiography, red-free, blue, red, near infrared, infrared, various types of auto-fluorescence at various wavelengths, and functional imaging such as flavoprotein auto-fluorescence and other fluorophores including those in the retinoid cycle.

2. Description of Related Art

Many comprehensive ophthalmologists and optometrists fail to fully utilize ophthalmic imaging devices (either traditional fundus cameras or imaging at the slit lamp) for a variety of reasons such as present day devices are expensive, image quality is poor, devices are difficult to align to a patient's eye, staff is not properly trained, images are not easily accessed, and overall device performance does not allow clinicians to realize the benefits and value of imaging. While physicians would always prefer a widely dilated pupil for retinal examination, this is not always possible or convenient for patients. Problems managing ghost and other reflections during examination, with undilated or dilated pupils, and lack of patient cooperation are common.

Adoption of retinal imaging devices (fundus cameras) historically has been largely in retina subspecialty where experienced technicians have been trained to operate complex equipment. While there has been some market expansion to general ophthalmology and optometry of non-mydriatic fundus cameras, device expense, ease of access, and complexity of operation have hindered the widespread adoption of current devices. Often these are separate free-standing devices that take up additional office space and are not convenient to the examination lane where primary eye exams are performed. Although many practices place existing devices in patient test areas, they are not highly utilized for all the reasons previously stated. Current slit lamp imaging systems are difficult to operate and do not eliminate specular reflections or other reflections from images. Additionally, lighting is not easily controlled and is sub-optimal for retinal imaging over a wide field. Fundus cameras employ an annulus to illuminate the retina and therefore require a larger pupil size to obtain images. These devices can be difficult to align to a patient's pupil.

Additionally, some systems today utilize a point source for illumination, but their field-of-view of the retina is severely limited, optical artifacts are often present, can be difficult to eliminate, and image quality is generally poor. Other systems use scanning laser systems which are expensive, and do not offer color imaging modes. Some scanning laser systems also suffer from central artifacts and other reflections. Scanning laser systems have been typically targeted at retina specialty due to specialized diagnostic functionality (fluorescein angiography, ICG Angiography and Auto-fluorescence).

With an aging population and significantly increased prevalence of eye disease, there is a large unmet need for cost-effective retinal imaging for the mass markets of ophthalmology and optometry that has automated features, is capable of imaging through small pupils, is easy to operate, and offers good image quality with artifact-free images.

SUMMARY OF THE INVENTION

In an exemplary embodiment of the present invention, there is disclosed a slit lamp mounted eye imaging device well suited for viewing wide field and/or magnified views of retinal images through an undilated or dilated pupil. The device is capable of imaging the anterior and posterior segments of the eye as well as sections/focal planes in between. The device contains a converging light illumination system, aperture stops, a controller and digital camera subsystem. The converging light illumination system may be made up of one or more light sources, or a single shifting or rotating light source, such as an LED, which can be delivered into the optical system either on the optical axis or slightly off axis from the center of the optical system and return imaging path(s) from the retina. The device provides entry of light rays into the eye, wide field retinal illumination, reduced glare, and elimination of artifacts and ghost reflections. Aperture stops, position of optics, and/or off-axis illumination blocks unwanted reflections or glare from being formed in the retinal image, however primary artifacts are not avoided, but rather removed through image processing and the acquisition of two or more images with artifacts in distinctly different locations. This image processing consists of automated detection of artifacts from one or more images, removal of artifacts and montage of two or more images to eliminate artifacts. The device is well suited for retinal viewing and imaging through an undilated pupil which is non-pharmacologically dilated or even as small as 2 mm provided the aperture and illumination is sized and positioned in accordance with the diameter of an undilated pupil. The adjustment of this aperture may be fixed or adjustable by the user. It may also auto-sense pupil size and self optimize size of aperture and illumination, as well as auto-sense optimal image capture triggering. While the device can be mounted to a slit lamp it can also be used on a separate chinrest and joystick assembly. Also, the device can utilize existing slit lamp optics, beam splitters, adapters and other elements, whereby containing illumination and optical aspects of this device in a separate housing to be attached to the slit lamp, while utilizing slit lamp imaging aspects and subsystem.

The foregoing has outlined, rather broadly, the preferred features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

DESCRIPTION OF THE PREFERRED EMBODIMENT

Figure 1:
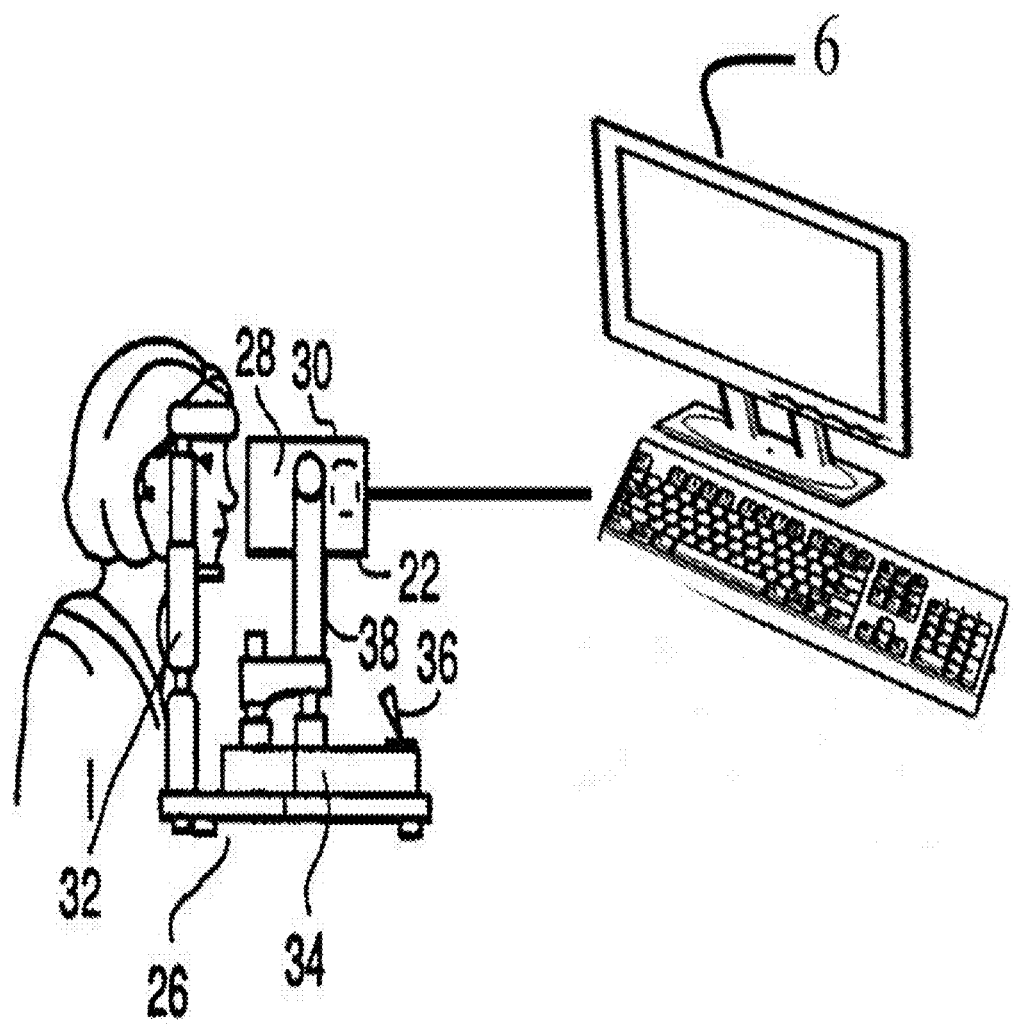
FIG. 1 is view of apparatus in accordance with the principles of the invention.

Retinal imaging has been traditionally performed with a fundus camera which uses an annulus of light to illuminate the retina, with the return image path coming back through the center of the illumination annulus. These devices often have complex illumination and imaging paths in order to allow the annulus to be as small as possible to accommodate a small pupil, while leaving ample aperture for imaging to pass back through the center, and to eliminate optical artifacts and reflections. This historical optical design was used to allow wider field imaging without reflections from the cornea and other surfaces. Traditional ophthalmoscopy (direct, indirect, slit lamp based or other) which have been based on a point source of illumination offer limited field of view if reflection-free images are desired. Retinal imaging systems based on point sources of light historically have only achieved a maximum of approximately thirty degree field of view, while still eliminating reflection and other artifacts. Other systems such as scanning laser ophthalmoscopes may offer wider field than simple point source based devices (like slit lamp retinal imaging) with the use of scanning mirrors and lasers. Yet other devices (Optos Optomap) achieve wide field imaging through small pupils with the use of a scanning system and large parabolic mirror. These solutions are often very costly and employ complex optical setups that control scanning elements and/or image capture elements. Historically the challenge has been to have the ability to cost-effectively image the retina that allows for small pupils, wider field of view (>40 degrees up to ultra wide field—200 degrees) and that this artifact and reflection free. The challenge has been to have a cost effective design that allows all of these parameters, and one that can be slit lamp mounted for ease of patient and doctor access. This invention solves each of the described problems through the combination of innovative optical design, light sources, coupled with image processing techniques that eliminate the problems as listed above.

The device disclosed can be used for imaging the eye, including but not limited to anterior segment imaging (cornea, lens, anterior chamber), posterior segment of the eye including modalities of color fundus, fluorescein angiography, ICG angiography, red-free, blue, red, near infrared, infrared, various spectral wavelengths of auto-fluorescence, and functional imaging (flavoprotein auto-fluorescence, fluorophores in the retinoid cycle, and others). It can be operated with high magnification, wide field of view or in a zoom mode, and in a plenoptic mode to allow various focal lengths to be combined into a composite image that can be sectioned through, or combined into a single image. The device may consist of one or more light sources and/or a shifting optical path (or elements therein) to achieve one or more images that contain artifacts or reflections in distinctly different anatomical locations, and to be combined into an artifact, reflection-free image. An eyecup with angular protrusions for holding eyelids open is provided to create a patient-device interface and darkened environment for operation in a myd and/or non-mydriatic mode.

The device disclosed is a low cost slit lamp (or separate chinrest-joystick assembly) eye imaging device well suited for viewing wide field and/or magnified views and generation of retinal images through an undilated or dilated pupil. It is also capable of imaging the anterior segment of the eye as well, and sections/focal planes in between. The device contains one or more illumination light sources, having LED, Halogen, Xenon, or other lamps and filters, and containing aperture stops for clean delivery of energy from one or more sources. The converging light illumination system may be made up of one or more light sources, where LED (of single and/or various wavelengths) is preferred, and can be delivered into the optical system either on the optical axis or slightly off the optical axis from the center of the optical system and return imaging path from the retina. The device directs light rays into the eye, and provides wide field retinal illumination and reduced glare. Aperture stops and/or off-axis illumination blocks unwanted reflections or glare from being formed in the retinal image. The device is well suited for retinal viewing through an undilated pupil as small as 2 mm provided the aperture and point source is sized in accordance with the diameter of the undilated pupil. The aperture may be fixed or adjustable by the user. It may also auto-sense the pupil size and self optimize the size of aperture. The device may turn on and off the LED or other light sources in a sequential manner which may be accompanied by a shift in the optical system of one or more of its optical elements or components to create two (or more) images with specular reflection and other artifacts located in two anatomically different areas of each of the sequentially acquired images.

In another embodiment one or more sources of illumination are provided with a lateral shift or rotation of the optical element(s) to shift the illumination and/or the field of view to illuminate and image a wider field of view on the retina. Also, when images are combined, a final image with more even illumination and greater image clarity can be obtained, analyzing each of the image areas from the various images, and utilizing those portions that offer the best focus, least aberrations, and best overall image quality. An image processing algorithm can be provided that automatically detects the primary reflection artifacts in the image and performs an image reconstruction function that uses the valid image information from the corresponding image(s) where the artifact was masking the retina in the source image. In place of strobing and combining images, the device may simply montage the images together after performing similar artifact removal from one or a series of images. This may also be accomplished with a patient's change in fixation in a random or a controlled or automated manner. The optical design may contain one or more light sources and may add a prism such as a half penta prism, a Schmidt prism or a custom prism that redirects the illumination and imaging paths to be slightly offset from each other to create overlapping illumination and images for increased field of view, that allow sections of the images to be combined for an artifact and reflection-free image. These alternate illumination and imaging paths may enter the eye pupil in an angular way compared to the optical center or may enter slightly off axis but parallel to the center of the optical system. The angle of separation of these various overlapping light sources and imaging paths may be variable depending upon the pupil size and may adjust automatically based upon automated with detection of the size of the pupil.

Another embodiment of the device adapts to a slit lamp and utilizes exiting commercially available components such as beam splitters, adapters, other optics, digital and video cameras for image capture on the slit lamp. In this configuration illumination, light sources, and additional optics are incorporated into a separate housing that could attach to the slit lamp in a variety of ways including tonometer post, rhuby glide plate mount, or other mechanical connection on the slit lamp. This embodiment would separate out the illumination and optical aspects of the device from the image capture aspects of the device for mounting on a slit lamp, thereby utilizing the existing slit lamp capture capability, while still providing the unique optical, illumination and image processing aspects of the device.

The device can have a manual focus and/or an autofocus mechanism. An automatic exposure algorithm and image brightness and contrast optimization algorithm can be provided to optimize image quality. An alignment mode in either the visible, NIR, or IR is provided that allows a user to align to the retina or the external pupil. The device may contain an optical and image processing alignment aid that guides the user toward optimal alignment. The device can contain an automated or manual alignment algorithm and mechanical control for aligning a pupil of the eye along an optical axis to the patient's pupil. The device can contain a spatial light modulator for positioning and shaping the illumination beam according to the sensed location and dimensions of the pupil and may measure and record the pupil size. The device can employ an IR or near IR filter that is positioned in place for an alignment mode and flipped out to allow other spectral wavelengths to pass and for subsequent image capture.

In an embodiment an anti-shake optical and/or other image stabilization software algorithm can be provided to automatically align the device to the patient's eye and also ease alignment of images for averaging and other image processing and viewing functions.

The device as described above can contain a wireless sd card or other embedded wireless technology for automatically transmitting images to a host computer or other storage device or software. The device can contain a "name tag mode" which will allow the user to take an image of the patient's name, perform optical character recognition, detect first name, last name and chart code, know the date and time, (and other data) and automatically populate a database with this information, all transmitted to the host. This can be performed by an embedded processor in the device or by a host computer.

The system described may also utilize a flexible eye cup that can be fixed to the device, or as a consumable item that attaches to the end of the device for use on each patient. The eye cup can be made of baffled flexible material of rubber, plastic, or any other soft material that surrounds the patient's eye to create a darkened environment. The eye cup can also be used to hold the eye lid open, perhaps through an angular internal spring mechanism that presses on the eyelid and holds it open. The baffles can be flexible to allow for proper positioning to the eye. One embodiment of the eye cup contains a firm rubber or plastic portion located at approximately the twelve o'clock and six o'clock positions that angularly protrudes and that is used to hold the upper and/or lower eyelids open during imaging. The rest of the eyecup covers the eye to create a darkened environment for natural pupil dilation. The device can also contain an infrared or near-infrared LED or other light source coupled with a detector such as a CCD, CMOS, or other device that is sensitive to light at this wavelength. This will be used for alignment, but turned off and the patient will be flashed with visible light, green light, blue light, red-free, or any other wavelengths for imaging including fluorescein angiography, ICG angiography, fundus auto-fluorescence or other wavelengths used in other auto-fluorescence or functional imaging.

The device can have all of the embodiments as described above plus the ability to create a multi-focal plenoptic image, an image or movie that is created from images at multiple focal planes. This image can be formed by a camera system (that may contain one or more cameras) that has micro-lenses over the top of a CCD or CMOS pixel array and divided into two or more focal plans. This image will be calibrated and reconstructed into a multi-focal plenoptic image. Alternatively, a plenoptic multi-focal image can be created by using a manual or auto-focus mechanism that finds the optimal center focus and then acquires additional images with slight focus adjustments bracketed around the center focal point. These images can then be combined into a single plenoptic image or combined into an interactive movie image that allows the user to scroll through multiple focal planes. The algorithm to combine images would automatically align the images while correcting for translation, rotation, curvature, and magnification differences between the images. The software would detect high frequency information in each image plane corresponding to each optimal image plane. The plenoptic algorithm could also be used for combining images of different modalities. For example, ICG images highlighting choroidal detail can be combined with Fluorescein angiography images highlighting retinal detail. The plenoptic algorithm can be used for any combination of retinal images or retinal imaging modalities such as optical coherence tomography (OCT) and/or other modalities from other retinal imaging devices. The algorithm can also be applied to images from multiple focal planes in the anterior segment of the eye. One embodiment would allow for continuous capture of images through the entire eye from anterior to posterior and allow for application of the algorithm to combine into a single plenoptic image or movie loop viewing function of the entire eye, or portions thereof, including registration and alignment with other modalities.

The device and all its embodiments could consist of components, light sources and filters that allow all retinal types of retinal imaging including but not limited to color fundus imaging, red-free, ICG angiography, fluorescein angiography, IR, or near IR imaging, all forms of fundus auto-fluorescence at various wavelengths, and functional imaging.

In another embodiment of the device the user programs an internal fixation target for the patient to follow and then stitches images together as they are captured. This would also be applied for artifact removal. Multiple images can be stored as a movie file, single frames or a single frame stitched together. In another embodiment of the device interchangeable objective lenses are provided for different fields of view and also for anterior segment imaging through slit shaped illumination and other form factors for optimal anterior segment imaging.

In another embodiment of the device a lens, stops and masking are optimized for retro-illumination imaging of the eye lens and other eye features.

Another embodiment of the device allows for incorporation with optical coherence tomography (OCT) systems, for purposes of retinal imaging in combination with OCT.

Another embodiment of the device performs a dark-correction algorithm whereby an image by the CCD or CMOS chip is captured in a darkened environment and this noise field image is processed, stored and subtracted from captured images as a means to reduce noise and improve overall image quality.

Another embodiment of the device allows it to be operated in a switchable normal focus or plenoptic mode to allow for capture of images from multiple focal planes.

Another embodiment of the device has a stereo optical system for real time or processed single image stereoscopic view. This is achieved in a variety of different ways including optical shift, CCD multi-focal lens overlay, and microlens overlay derived from video scanning, motion and/or focus.

Another embodiment of the device is an alternative to rapid alternate strobing of an LED or multiple LED's, but rather a rotation of an optic at a rapid rate that is synchronized with the image capture.

Another embodiment is a rotating or shifting light source. This can be done with several optical elements in the system or even with a rapidly rotating (synchronized) optic like a wedge prism. The artifact would be mapped to the other image in the pair to remove the artifact. This could be done in image process or even with a calibration and real-time memory mapping, or single image capture. This also serves as a means of increasing the field of view of the image and can be put together in a panorama as a single image with artifacts removed.

Another embodiment of the device uses any or all of the described elements and stitches a panorama together in real time from the video stream.

The video/digital camera 22, the and optics 29 form an optical subsystem of the apparatus 2 and are located in a common housing 30, see FIG. 1 which is mounted on a slit lamp chinrest and joystick assembly 26.

Referring to FIG. 1, slit lamp chinrest and joystick assembly 26 is a device for interfacing the video/digital camera 22, illumination source(s) optics 28 to the patient's eye. Slit lamp chinrest and joystick assembly 26 comprises head support 32, movable base 34, joystick 36, and housing support 38. The head support 32 holds the patient's chin and forehead in a known, fixed position. The head support 32 is provided with elevation adjustments to provide a comfortable resting place for the patient's head. The position of housing 30 relative to the head support 32 can be adjusted in both gross and fine increments using the joystick 36.

Figure 2:
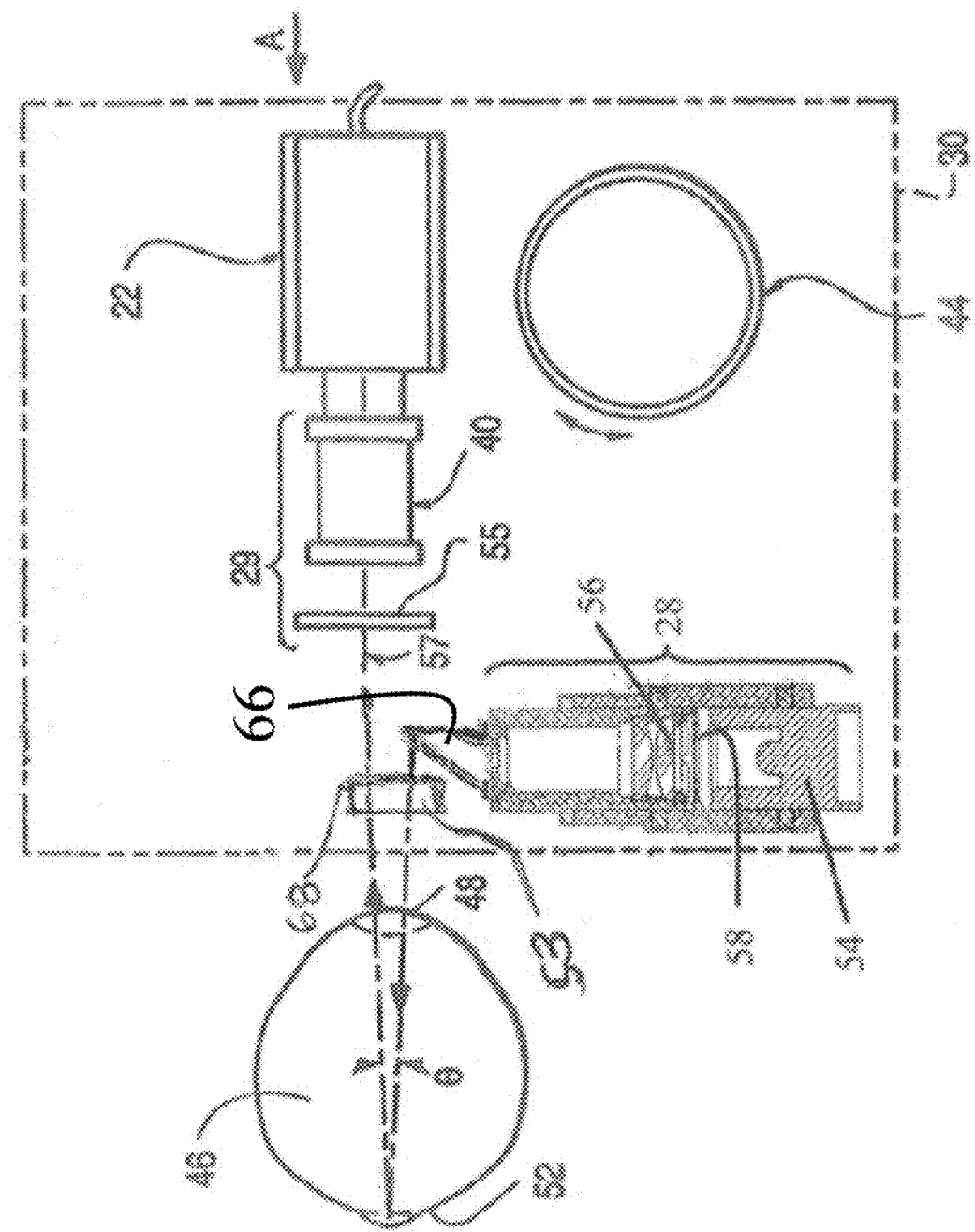
FIG. 2 is a side view of an optical unit of the chinrest and joystick assembly of the present invention.

FIG. 2 is a side view diagram of an optical unit of the chinrest and joystick assembly of the present invention. In FIG. 2, the housing 30 containing the video/digital camera 22, illumination source(s) and optics 28 is shown in side sectional view, proximate to a sectioned eyeball 46 having a cornea 48 and a retina 52. Housing 30 may be cylindrical or of another appropriate shape.

As will be seen, the structure of housing 30, which has no forward protruding parts, prevents accidental direct contact of any part of the apparatus with the patient's cornea or facial features during movement of the housing 30 relative to the patient's eyes. This feature of the present invention is particularly advantageous in that a number of prior art methods of acquiring optic data require that optics approach and/or contact with the cornea to accomplish the tasks of examination and image capture. The external housing 30 and the optics therein, by contrast, have been designed to maintain some distance to the cornea, increasing patient comfort while the test is being performed. If desired, a flexible interface such as a rubber cup can be provided at the interface between the housing 30 and the patient's eye.

The inclusion of projection optics 28, observation optics 29 and video camera 22 in a single compact housing provides a high degree of accessibility. By placing all elements of the system in one housing, allows for an affordable design. Additionally, the miniaturization of design compared to that of a fundus camera for observation and image capture provides for a shorter and more efficient optical pathway. The compact design and simplicity of optics reduces production costs and permits greater ease of use by the operator. The design allows imaging through a smaller pupil as compared to a fundus camera.

Video/digital camera 22 is preferably compact and incorporates a monochrome CCD or CMOS image sensor. A manual override image focus knob 44 accessible from the back of housing 30 is connected to the lens 40 associated with video camera 22 by conventional optical gearing mechanisms to allow focusing of the lens 40. The focusing of lens 40 by means of image focus knob 44 will compensate for the optics of eye 46. Lens 40 may be focused automatically or manually by observing the image displayed on an observation video monitor while adjusting image focus knob 44 until a clear, focused image is obtained on the observation video monitor. Alternatively, an electronic auto-focusing control system could be provided for automatically adjusting the focus of lens 40.

The digital/video camera 22 can also contain a monochrome or color CCD or CMOS sensor.

The observation optics 29 associated with the video camera 22 include the aforementioned lens 40, an observation aperture 53, and a filter 55. The observation aperture 53 and the filter 55 transmit light reflected from the retina 52 to the lens 40 and hence to video camera 22. The filter 55 is an infrared blocking filter (or other filter for other imaging procedures) which improves the contrast of the image seen by the video camera 22.

If it is desired to use the apparatus 2, for indo-cyanine green angiography, color fundus photography, auto-fluorescence, or fluorescein angiography, additional filters may be provided as appropriate. These filters will be mounted so as to be selectively rotatable in and out of the view axis of the video camera 22 according to the function being performed. The rotation may be accomplished manually or under computer servo control.

Continuing with FIG. 2, the projection optics 28 of the invention projects light onto the retina 52, off axis at an angle to the central axis 57 of lens 40 of video camera 22. The projection optics 28 comprises a lamp 54, lamp lens group 56, optics 64, mirror 66, and projection aperture 68. A control (not shown) is provided to adjust the intensity of the lamp 54, either manually or under the control of personal computer 6, see FIG. 1. The control is also used to sequentially control multiple lamps, shifting optical elements such as 68, and image capture trigger.

Light from lamp 54 passes through aperture 58, and the series of lamp lens group 56 consisting of two lenses. The lenses of lamp lens group 56 concentrate the light output of lamp 54. Lamp lens group 56 may preferably consist of two achromatic lenses. The light is then deflected by mirror 66 which is placed at a critical pitch angle relative to the video camera 22 and the projection optics 29. The light passes from the mirror 66 through projection aperture and lens combination 68 which concentrates the light. The light then passes through the cornea 48 and is projected onto retina 52.

All the apertures used, such as apertures 58 and 68, are appropriately sized apertures. Although the lamp 54 has been described as a generalized LED lamp, it should be noted that the lamp 54 can be any source of radiant energy. In one preferred embodiment, the lamp 54 is an infrared illumination source, and the specifications of filter 55 are adjusted accordingly to pass the wavelength of the lamp 54. Infrared illumination may be particularly desirable for alignment prior to acquiring images without the problems generated by lack of pupil dilation. The image can be captured in a relatively dark room using infrared illumination, so that the eye being imaged is naturally dilated. In another preferred embodiment which addresses the problems caused by lack of pupil dilation during imaging, the lamp 54 may be strobed in full color, red free, NIR or some other preferred wavelength (based on imaging procedure desired) during image acquisition rather than being kept on constantly, thereby preventing the energy of lamp 54 from narrowing the pupil prior to image capture. Because of the unique design of the projection optics 28 and the capabilities of the image processing and analysis software employed, useful image data from each image can be collected with minimum pupil dilation. Specifically, the pupils of the eye being imaged may have a diameter of as little as 2 mm. The projection optics 28 of device projects light onto the retina 52 off axis from the observation path of video/digital camera 22.

The apparatus of the present invention is shown generally in FIG. 1. A personal computer 6 forms the center of the system, processing data and controlling the operation of other components of the system. Connected to the personal computer 6 is a video/digital camera 22. An observation video monitor which can be the screen of the personal computer, a slit lamp chinrest and joystick assembly 26, projection optics 28, and observation optics 29 are associated with the optical head 30.

The personal computer 4 is preferably a compact computer of relatively high processing power using a standardized operating system and having standardized card slots for interfacing peripheral equipment such as video board, printer and a monitor. The personal computer 6 will run customized software as will be described in detail later.

The monitor or screen of the personal computer will have very-high-resolution color graphics capability appropriate for displaying images under analysis.

The digitizing board accepts a digital file or video input from digital/video camera 22 and functions as a "frame grabber," Or display. That is, when activated by a signal from the personal computer 6, the digitizing board will collect video and/or digital data and images from video/digital camera 22 at that instant and store into digital data. The digital data produced is stored in memory and made available to personal computer 6 for analysis.

Figure 3:
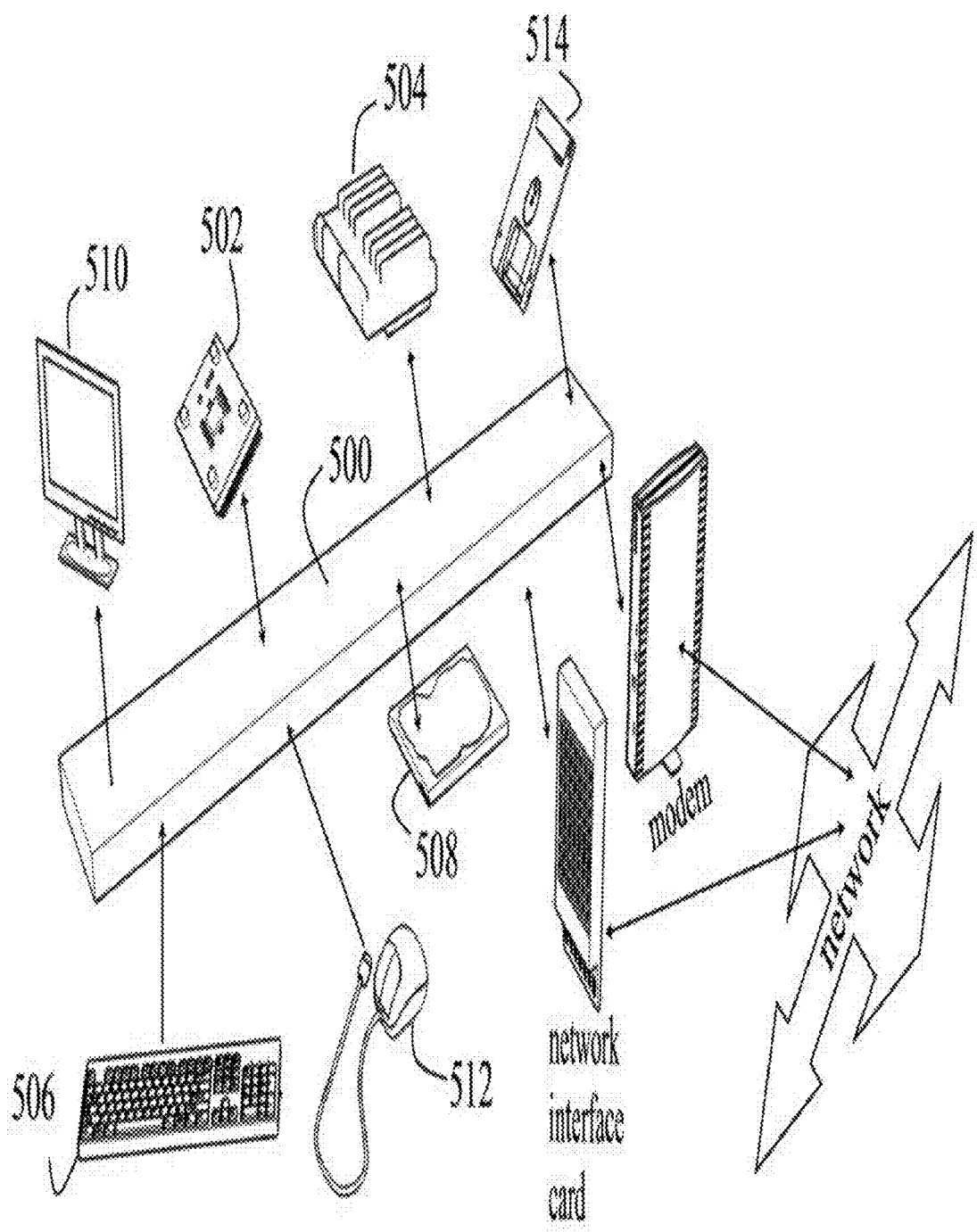
FIG. 3 is a block diagram of a computer system for use with the present invention.

The present invention can be used on any properly configured general purpose computer system, such as the system shown in FIG. 3. Such a computer system 500 includes a processing unit (CPU) 502 connected by a bus to a random access memory 504, a storage device 508, a keyboard 506, a display 510 and a mouse 512. In addition, there is a device 514 for entry of data and software, including software embodying the present invention, into the system. An example of such a computer can be a Dell personal computer operating on the Microsoft Windows operating system, or Linux, Macintosh, etc. The invention can also be used on a laptop computer, cell phone, PDA, etc.

The various method embodiments of the invention will be generally implemented by a computer executing a sequence of program instructions for carrying out the steps of the method, assuming all required data for processing is accessible to the computer. The sequence of program instructions may be embodied in a computer program product comprising media storing the program instructions. As will be readily apparent to those skilled in the art, the present invention can be realized in hardware, software, or a combination of hardware and software. Any kind of computer/server system(s)—or other apparatus adapted for carrying out the methods described herein—is suited. A typical combination of hardware and software could be a general-purpose computer system with a computer program that, when loaded and executed, carries out the method, and variations on the method as described herein.

The present invention may be embodied as a system, method, or computer program product. Accordingly, the present invention may take the form of a hardware embodiment, a software embodiment, or an embodiment combining software and hardware. Furthermore, the present invention may take the form of a computer program product embodied in any tangible medium of expression having computer-usable program code embodied in the medium.

Any combination of one or more computer usable or computer readable medium(s) may be utilized. Specific examples of the computer-readable medium can include: a hard disk, a random access memory (RAM), a read-only memory (ROM), an erasable programmable read-only memory (EPROM), or Flash memory, a portable compact disc read-only memory (CD-ROM), etc. In the context of this document, a computer-usable or computer-readable medium may be any medium that can be used by or in connection with the instruction execution system or apparatus. Computer program code for carrying out operations of the present invention may be written in any combination of one or more programming languages. The program code may execute entirely on the user's computer, partly on the user's computer, as a stand-alone software package, partly on the user's computer and partly on a remote computer or entirely on the remote computer or server.

The present invention is described above with reference to a computer program according to an embodiment of the invention. It will be understood that each block, and combinations of blocks shown, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart or blocks.

These computer program instructions may also be stored in a computer-readable medium that can direct a computer or other programmable data processing apparatus to function in a particular manner, such that the instructions stored in the computer readable medium produce an article of manufacture including instructions means which implement the function specified in the blocks.

The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions specified.

The flowchart in the figure illustrates the architecture, functionality, and operation of possible implementations of systems, methods and computer program products according to various embodiments of the present invention. In this regard, each block in the flowchart may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact be executed substantially concurrently, or the blocks may sometimes be executed in the reverse order, depending upon the functionality involved. It will also be noted that each block of the flowchart illustration, and combinations of blocks in the flowchart illustration, can be implemented by special purpose hardware-based systems that perform the specified functions or acts, or combinations of special purpose hardware and computer instructions.

Figure 4:
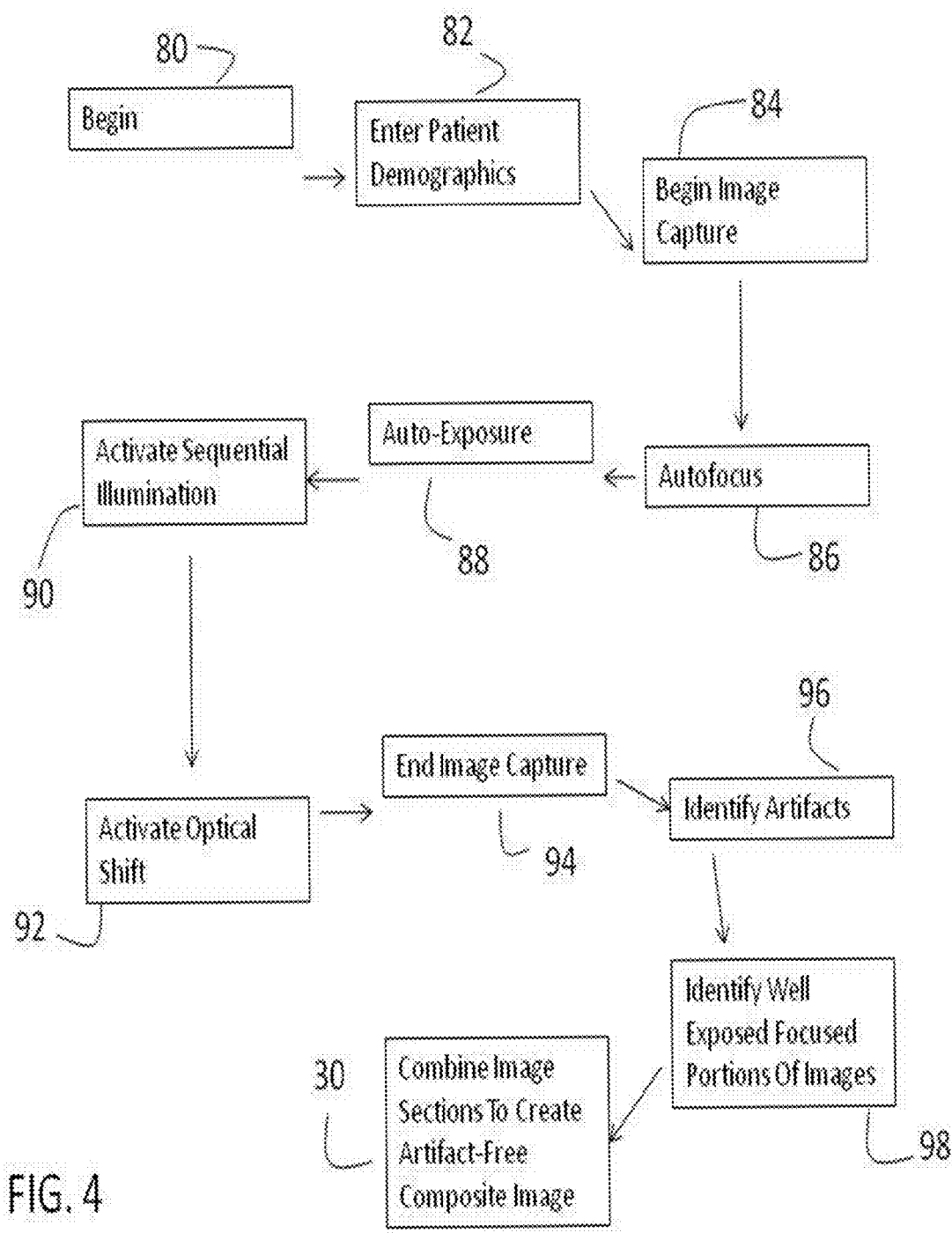
FIG. 4 is a flow chart showing steps of image capture and image processing algorithm in accordance with the principles of the invention.

FIG. 4 is a flow chart showing the steps of the image processing algorithm in accordance with the principles of the invention. In describing the various steps, reference is made to numbered parts in FIGS. 2 and 3. In the first step, 80, the program begins and advances to block 82 where the patient's demographics are entered. In block 84, image capture is begun. The software awaits an indication that the patient is prepared and the optics are focused. The patient places his or her head in the slit lamp chinrest and joystick assembly 26 so that the patient's head is held substantially immobile. The operator adjusts the position of housing 30 using adjustments on the chinrest and joystick assembly 26 and particularly using the joystick 36 until the projection optics 28 and the video camera 22 are aimed through one or the other of the patient's corneas 48 of the eye 46. Then in block 84, image capture is begun. Image capture is triggered by the operator or automatically by the computer based on algorithm for optimal image alignment by the operator pressing a button on the joystick, bluetooth keypad, or triggering a foot pedal to signal the device that the image of video/digital camera 22 should be recorded. Thereafter autofocus procedure, block 86, and auto-exposure procedure, block 88, are executed to obtain a clear image of the retina 52. In the next step sequential illumination is activated, block 90, and then optical shift is activated, block 92. Subsequently image capture is ended, block 94, and artifacts are identified, block 96. After identifying artifacts, well exposed focused portions of images are identified, block 98, and image sections are combined to create an artifact-free composite image, block 100. In response to the indication of the operator (or via controller) that the image should be recorded, the personal computer 4 will cause the image of video/digital camera 22 to store digital data representing the captured image(s).

In the embodiment described images that contain artifacts in different areas are captured—the artifacts are in different areas because the optics are shifted or they are multiple light sources in different locations in the optical design that generate artifacts in different location in the images. Those artifacts are detected and only combine the good quality portions of the images that are captured.

While there have been shown and described and pointed out the fundamental novel features of the invention as applied to the preferred embodiments, it will be understood that various omissions and substitutions and changes of the form and details of the apparatus illustrated and in the operation may be done by those skilled in the art, without departing from the spirit of the invention.

What is claimed is:

1. Apparatus for imaging the posterior and anterior segments of a person's eye comprising:
   a light source;
   an optical system having optical elements that can be shifted for delivering light from said light source either on optical axis or slightly off axis from the center of the optical system and return imaging path from the retina or other eye features;
   control means coupled to sequentially turn said light source on and off in synchronization with image capture under each condition; and
   means for shifting at least one of said optical elements in said optical system;
   wherein two images having specular reflection artifacts located in two anatomically different areas of each sequentially acquired image of said segment of the eye are created, and whereby the artifacts in each image are detected by image processing;
   wherein images with artifacts are combined with one or more images to create a composite image or video stream that is free of artifacts;
   wherein only clear well-focused image sections are combined from one or more images to create a composite image.

2. The apparatus of claim 1 wherein said light source is laterally shifted.

3. The apparatus of claim 2 wherein said light source is shifted and also rotated.

4. The apparatus of claim 3 wherein said light source has at least two or more light sources that are sequentially triggered.

5. The apparatus of claim 3 wherein the alternate illuminating and imaging paths enter the eye pupil at an angle compared to the optical center axis but parallel to the center of the optical system.

6. The apparatus of claim 5 wherein the angular separation of the overlapping light sources and imaging paths are of variable size position and shape depending upon pupil size and can be manually or automatically adjusted based on pupil size.

7. The apparatus of claim 6 wherein a spatial light modulator is provided for positioning and shaping the illumination beam according to the sensed location and dimensions of the pupil.

8. The apparatus of claim 6 wherein an IR or near IR filter is provided for alignment mode and flipped out to allow other spectral wavelengths to pass and subsequent image capture.

9. The apparatus of claim 6 wherein a flexible eye cup of flexible material positioned to surround a person's eye to create a darkened environment and to hold a person's eyelids open during eye imaging;
   wherein the eye cup contains a hardened portion at the 12 o'clock and/or 6 o'clock positions and presses in and upward and downward 45 degree angular direction, that is used to hold eyelids open.

10. The apparatus in claim 6 wherein the focus of the device is varied and stepped to allow capture at multiple focal planes in the eye, and recombined into a single plenoptic image and movie.

11. The apparatus in claim 6 where the focus of the device is varied by a series of microlenses of differing focal lengths is placed on an image sensor and images subsequently captured at multiple focal lengths.

12. The apparatus in claim 11 that attaches to an existing slit lamp or fundus camera and utilizes a portion of said imaging elements and system for image capture and image processing.

13. The apparatus in claim 12 that is fitted with light sources and filters for procedures of color fundus imaging, fluorescein angiography, red-fee-red, blue, ICG angiography, all wavelengths of autofluorescence, functional imaging, lens, cornea and other anterior segment imaging, tear film imaging, optical coherence tomography, and ultra-wide field imaging, and as a guidance system for various treatment modalities.

14. The apparatus of claim 1 wherein said light source is rotated.

15. A method of imaging the posterior and anterior segments of a person's eye comprising the steps of:
providing a light source;
providing an optical system having optical elements that can be shifted for delivering light from said light source either on optical axis or slightly off axis from the center of the optical system and return imaging path from the retina or other eye features;
providing control means to sequentially turn said light source on and off in synchronization with image capture under each condition; and
providing means for shifting at least one of said optical elements in said optical system;
wherein two images having specular reflection artifacts located in two anatomically different areas of each sequentially acquired image of said segment of the eye are created, and whereby the artifacts in each image are detected by image processing;
wherein images with artifacts are combined with one or more images to create a composite image or video stream that is free of artifacts;
wherein only clear well-focused image sections are combines from one or more images to create a composite image.

16. The method of claim 15 wherein said light source is laterally shifted.

17. The method of claim 16 wherein said light source is shifted and also rotated.

18. The method of claim 17 wherein said light source has at least two or more light sources that are sequentially triggered.

19. The method of claim 18 wherein the alternate illuminating and imaging paths enter the eye pupil at an angle compared to the optical center axis but parallel to the center of the optical system.

20. The method of claim 19 wherein the angular separation of the overlapping light sources and imaging paths are of variable size position and shape depending upon pupil size, and can be manually or automatically adjusted based on pupil size.

21. The method of claim 20 wherein a spatial light modulator is provided for positioning and shaping the illumination beam according to the sensed location and dimensions of the pupil.

22. The method of claim 21 wherein an IR or near IR filter is provided for alignment mode and flipped out to allow other spectral wavelengths to pass and subsequent image capture.

23. The method of claim 22 wherein a flexible eye cup of flexible material positioned to surround a person's eye to create a darkened environment and to hold a person's upper eyelid open during an eye imaging wherein the eye cup contains a hardened portion at the 12 o'clock and/or 6 o'clock positions and presses in and upward and downward 45 degree angular direction, that is used to hold eyelids open.

24. The method of claim 23 wherein the focus of the device is varied and stepped to allow capture at multiple focal planes in the eye, and recombined into a single plenoptic image and movie.

25. The method of claim 24 wherein the focus of the device is varied by a series of microlenses of differing focal lengths is placed on an image sensor and images subsequently captured at multiple focal lengths.

26. The method of claim 25 wherein attaching to an existing slit lamp or fundus camera and utilizes a portion of said imaging elements and system for image capture and image processing.

27. The method of claim 26 fitting with light sources and filters for procedures of color fundus imaging, fluorescein angiography, red-free, blue, red, ICG angiography, all wavelengths of autofluorescence, functional imaging, lens, cornea and other anterior segment imaging, tear film imaging, optical coherence tomography, and ultra-wide field imaging, and as a guidance system for various treatment modalities.

28. The method of claim 27 containing a lateral shift of optical elements to create a three dimensional stereo pair of images.

29. The method of claim 28 containing an anti-shake/image stabilization algorithm for removal of eye movement and operator movement.

30. The method of claim 29 automatically building a wide field panoramic image during or just after image capture, building upon the previously captured images, to create a large panoramic view of the retina or other eye anatomy and features.

31. The method of claim 30 containing a means for controlling patient fixation and thereby creating images with artifacts in different anatomical locations and thereby combing said images into artifact-free composite images.

32. The method of claim 15 wherein said light source is rotated.

* * * * *